(12) United States Patent
Liu

(10) Patent No.: US 12,053,245 B2
(45) Date of Patent: Aug. 6, 2024

(54) APPARATUS AND METHOD FOR REAL-TIME OBJECT MONITORING

(71) Applicant: MEDICAL INTELLIGENCE MEDIZINTECHNIK GMBH, Schwabmunchen (DE)

(72) Inventor: Rui Liu, Schwabmunchen (DE)

(73) Assignee: MEDICAL INTELLIGENCE MEDIZINTECHNIK GMBH, Schwabmünchen (DE)

( * ) Notice: Subject to any disclaimer, the term of this patent is extended or adjusted under 35 U.S.C. 154(b) by 588 days.

(21) Appl. No.: 17/296,178

(22) PCT Filed: Dec. 6, 2019

(86) PCT No.: PCT/EP2019/083997
§ 371 (c)(1),
(2) Date: May 21, 2021

(87) PCT Pub. No.: WO2020/115280
PCT Pub. Date: Jun. 11, 2020

(65) Prior Publication Data
US 2022/0008138 A1 Jan. 13, 2022

(30) Foreign Application Priority Data
Dec. 6, 2018 (EP) .................................. 18210832

(51) Int. Cl.
*A61B 34/20* (2016.01)
*A61B 90/00* (2016.01)
(Continued)

(52) U.S. Cl.
CPC .............. *A61B 34/20* (2016.02); *A61B 90/39* (2016.02); *A61B 90/98* (2016.02); *H01Q 3/30* (2013.01);
(Continued)

(58) Field of Classification Search
CPC ...... A61B 2090/397; A61B 2090/3975; A61B 90/39; A61B 90/98; A61B 2034/2046;
(Continued)

(56) References Cited

U.S. PATENT DOCUMENTS 6,249,212 B1 * 6/2001 Beigel ................ G06K 19/0723
340/10.41
8,816,857 B2 * 8/2014 Nordin ............... G06K 7/10336
340/572.1
(Continued)

FOREIGN PATENT DOCUMENTS

EP 1229342 A2 8/2002

OTHER PUBLICATIONS

International Searching Authority. International Search Report and Written Opinion for application PCT/EP2019/083997. Mailed on Feb. 4, 2020. 11 pages.
(Continued)

*Primary Examiner* — Carolyn A Pehlke
(74) *Attorney, Agent, or Firm* — QUARLES & BRADY LLP

(57) ABSTRACT

The present disclosure provides an apparatus for determining a location of a wireless marker for a tumor, the apparatus comprising: a phased array antenna, and a processor, wherein the processor is configured to control the phased array antenna to transmit a wireless signal to the wireless marker, receive a wireless signal transmitted by the wireless marker in response to the transmitted wireless signal, and analyze the wireless signals transmitted and received by the phased array antenna to determine a location of the wireless marker. The present disclosure also provides a method for determining a location of a wireless marker for a tumor, wherein the method comprises: transmitting, using a phased antenna array, a wireless signal to the wireless marker,
(Continued)

receiving, at the phased antenna array, a wireless signal transmitted by the wireless marker in response to the transmitted wireless signal, and analyzing the wireless signals transmitted and received by the phased array antenna to determine a location of the wireless marker.

13 Claims, 6 Drawing Sheets

(51) Int. Cl.
 *A61B 90/98* (2016.01)
 *H01Q 3/30* (2006.01)
(52) U.S. Cl.
 CPC ............ *A61B 2034/2051* (2016.02); *A61B 2034/2072* (2016.02); *A61B 2090/3908* (2016.02); *A61B 2090/3975* (2016.02)
(58) Field of Classification Search
 CPC .... A61B 2034/2051; A61B 2034/2072; A61B 34/20; H01Q 3/30
 See application file for complete search history.

(56) References Cited

U.S. PATENT DOCUMENTS

| | | |
|---|---|---|
| 9,248,003 B2 | 2/2016 | Wright |
| 2007/0080787 A1* | 4/2007 | Taki ................... G06K 7/10316 340/572.1 |
| 2007/0167739 A1 | 7/2007 | Salo |
| 2010/0109848 A1* | 5/2010 | Blair ...................... A61B 90/98 340/10.2 |
| 2010/0275934 A1 | 11/2010 | Keren |
| 2012/0203306 A1 | 8/2012 | Sarvazyan |
| 2016/0294040 A1* | 10/2016 | Blair ........................ H01Q 7/00 |
| 2016/0302772 A1 | 10/2016 | Cummins |
| 2017/0272123 A1 | 9/2017 | Zhu |

OTHER PUBLICATIONS

European Patent Office. Extended European Search Report for application 18210832.4. Mailed on Jun. 12, 2019. 8 pages.

* cited by examiner

APPARATUS AND METHOD FOR REAL-TIME OBJECT MONITORING

CROSS-REFERENCE TO RELATED APPLICATIONS

This application is a U.S. National Phase of International Application No. PCT/EP2019/083997 filed Dec. 6, 2019 which claims the benefit of priority to Application No. EP18210832.4 filed on Dec. 6, 2018, which are herein incorporated by reference in their entirety.

FIELD OF DISCLOSURE

The present disclosure relates to an apparatus and a method for determining the location of a wireless marker.

BACKGROUND OF THE DISCLOSURE

Real-time positioning and tracking a tumor inside a patient's movable tissue (e.g., lung, prostate) is a challenging area in the medical industry and especially in radiation therapy. Various imaging guided approaches have been developed to track a tumor inside patients, for example ultrasound and magnetic resonance. However, these approaches are expensive and the field of view (FoV) is very limited. Moreover, it needs complex real-time imaging reconstruction method to track tumor location due to respiration, organ filling, cardiac conditions, etc.

SUMMARY OF THE DISCLOSURE

Recent developments have been made to track an implanted device based on the generated electromagnetic (EM) field, for example biomarkers, close to a patient's tumor to report isocenter location during radiation treatment. While some systems such as disclosed in U.S. Pat. No. 9,248,003 can provide millimeter rage accuracy using wireless receivers, these systems also have significant drawbacks. For example, the wireless transceiver is required to be placed on top of the patient, which seriously limits its usage for patients with large body size, as well as navigation volume being limited by the generated magnetic field. Moreover, it blocks the beam path during radiotherapy. Other disadvantages include the patient being exposed to a significantly high dose of EM radiation and lots of EM energy is wasted due to the antenna impedance mismatch. Therefore, there is a need for a system which accurately detects and tracks a wireless marker already implanted near the patient's tumor while reducing the EM radiation to which the patient is exposed. It is the object of the present disclosure to overcome these drawbacks.

The present disclosure provides an apparatus for determining a location of a wireless marker, for example, the marker being for a tumor, the apparatus comprising: a phased array antenna, and a processor, wherein the processor is configured to control the phased array antenna to transmit a wireless signal to the wireless marker, receive a wireless signal transmitted by the wireless marker in response to the transmitted wireless signal, and analyze the wireless signals transmitted and received by the phased array antenna to determine a location of the wireless marker.

The present disclosure further provides a method for determining a location of a wireless marker, for example, the marker being for a tumor, wherein the method comprises: transmitting, using a phased antenna array, a wireless signal to the wireless marker, receiving, at the phased antenna array, a wireless signal transmitted by the wireless marker in response to the transmitted wireless signal, and analyzing the wireless signals transmitted and received by the phased array antenna to determine a location of the wireless marker.

DETAILED DESCRIPTION

Figure 1:
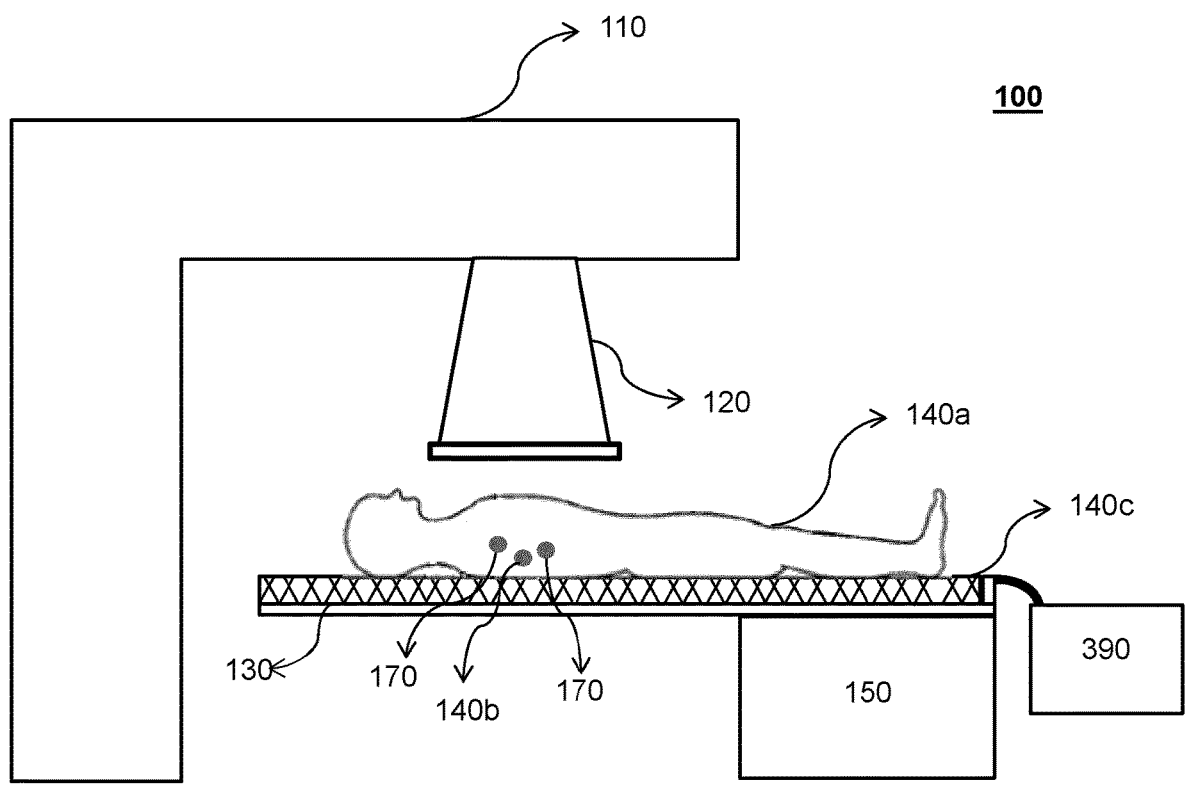
FIG. 1 is a radiation therapy apparatus in accordance with the present disclosure.

The apparatus and method of the present disclosure use a phased array antenna, and a processor configured to control the phased array antenna to transmit a wireless signal to the wireless marker, receive a wireless signal transmitted by the wireless marker in response to the transmitted wireless signal, and analyze the wireless signals transmitted and received by the phased array antenna to determine a location of the wireless marker.

According to some of the example embodiments, the processor is configured to control the phased array antenna to transmit a command to the wireless marker, and receive in response to the transmitted command, a unique digital ID of the wireless marker.

The processor can be further configured to identify an impedance of the phased array antenna, based on the unique identifier of the located wireless marker and adjust the impedance of the phase array antenna to control the signal strength of the transmitted and the received wireless signals.

According to some of the example embodiments, the processor is configured to activate the wireless marker, using the received unique digital ID, to transmit the wireless signal in response to the wireless signal transmitted by the phased array antenna, and initialize the phased array antenna based on an approximate location of the active wireless marker. According to some of the example embodiments, the processor sends instructions to adjust the impedance of wireless marker to further compensate antenna mismatch effects.

The processor can be further configured to receive, in response to the transmitted command, a unique digital ID of a further wireless marker, and deactivate the further wireless marker using the received unique digital ID of the further wireless marker.

The processor can also be configured to deactivate the wireless marker using the received unique digital ID of the wireless marker, activate the further wireless marker using the received unique digital ID of the further wireless marker, and transmit a wireless signal to the further wireless marker, receive a wireless signal transmitted by the further wireless marker in response to the transmitted wireless signal, and analyze the wireless signals transmitted and received by the phased array antenna to determine a location of the further wireless marker.

The apparatus of the present disclosure may also comprise a ferromagnetic layer, configured to be placed between the phased array antenna and the patient table. According to some of the example embodiments, the ferromagnetic layer comprises a plurality of sintered ferrite sheets. The purpose is to further reduce the EM energy loss due to the possible conductive material from patient table. Optionally, there may also be included an insulating mattress layer wherein the insulating mattress is configured to be placed between the patient and the phased array antenna. The purpose is to provide a buffer layer such that it can reduce the possible X-Ray imaging artifacts from conductive material inside phase array antenna and/or ferromagnetic layer, it also reduces the sensitivity of antenna mismatch due to short distance between patient's body and phase array antenna.

The phased array antenna of the present disclosure may comprise has a planar structure and is configured to be positioned on top of a patient support. The planar structure of the phased array antenna can be implemented on a printed circuit board (PCB) and/or a low temperature cofired ceramic (LTCC).

According to some of the example embodiments, the phased array antenna is configured to operate between 110 KHz and 2.5 GHz, for example, greater than 600 MHz or even 900 MHz.

The wireless marker of the present disclosure can be configured to be implanted within the body of a patient or to be attached to a surface of the patient.

The method of the present disclosure provides transmitting, using the phased antenna array, a wireless signal to the wireless marker, receiving at the phased antenna array a wireless signal transmitted by the wireless marker in response to the transmitted wireless signal, and analyzing the wireless signals transmitted and received by the phased array antenna to determine a location of the wireless marker.

According to some of the example embodiments, the method further comprises transmitting a command to the wireless marker, and receiving in response to the transmitted command, a unique digital ID of the wireless marker. The method may further comprise identifying an impedance of the phased array antenna, based on the unique identifier of the located wireless marker, and adjusting the impedance of the phased array antenna to control the signal strength of the transmitted and the received wireless signals. This may also entail activating the wireless marker using the received unique digital ID, to transmit the wireless signal in response to the wireless signal transmitted by the phased array antenna, and initializing the phased array antenna based on an approximate location of the active wireless marker. According to some of the example embodiments, the processor sends instructions to adjust the impedance of wireless marker to further compensate antenna mismatch effects. According to some of the example embodiments, the method further comprises receiving in response to the transmitted command a unique digital ID of a further wireless marker, and deactivating the further wireless marker using the received unique digital ID of the further wireless marker.

In a particular embodiment, the method further comprises deactivating the wireless marker using the received unique digital ID of the wireless marker, activating the further wireless marker using the received unique digital ID of the further wireless marker, and transmitting a wireless signal to the further wireless marker, receiving a wireless signal transmitted by the further wireless marker in response to the transmitted wireless signal, and analyzing the wireless signals transmitted and received by the phased array antenna to determine a location of the further wireless marker.

FIG. 1 describes a system 100 for real-time tumor location tracking. The system 100 comprises a beam generator 120, a support structure 110, a signal sensing unit 390 and a platform 150. The platform 150 supports a patient table 130. The patient table 130 is, for example, planar in structure and is arranged to support a patient 140a. The location of at least one tumor 170, for example, located inside the patient 140a, is monitored by means of the conventional beam generator 120. Additionally, at least one wireless marker 140b is implanted on the patient 140a and is located near the tumor 170.

According to some of the example embodiments, the implanted at least one wireless marker 140b is battery-less and purely powered by the signal sensing unit 390. The signal sending unit 390 transmits and receives signal which may contain a unique digital number which is used by a user to differentiate between the at least one each wireless marker 140b. Optionally, a type of wireless marker may also be differentiated using this information.

Optionally, a non-implanted wireless marker 140b may also be developed as a non-invasive way for body positioning and real-time tracking (e.g., place wireless markers 140b on the breast or nose, wherein the hardware is slightly modified such that it can be powered externally (e.g. using button-battery) to enhance the communication range and tracking accuracy.

The patient table 130 includes a main unit and, optionally, a subsidiary unit (not shown in FIG. 1). The patient table 130 is connected to a signal sensing unit 390. The main unit contains a set of array antennas 210 (not shown in FIG. 1) wherein the set of arrays antenna 210 are configured to receive and transmit a radio frequency signal. The signal sensing unit 390 contains a processor to process the received radio frequency signals and process data.

According to some of the example embodiments, the processor is configured to control the array antenna to transmit a command to the wireless marker 140b, and receive, in response to the transmitted command, a unique digital ID of the wireless marker 140b.

According to some of the example embodiments a phase array antenna 210 is configured to be positioned on top of a patient table 130.

According to some of the example embodiments the planar structure further comprises a ferromagnetic layer, optionally a ferrite sheet, wherein the ferromagnetic layer is configured to be placed between the phased array antenna 210 and the patient table 130.

Optionally the planar structure further comprises an insulating mattress layer wherein the insulating mattress is configured to be placed between the patient 140a and the phased array antenna 210.

Figure 2:
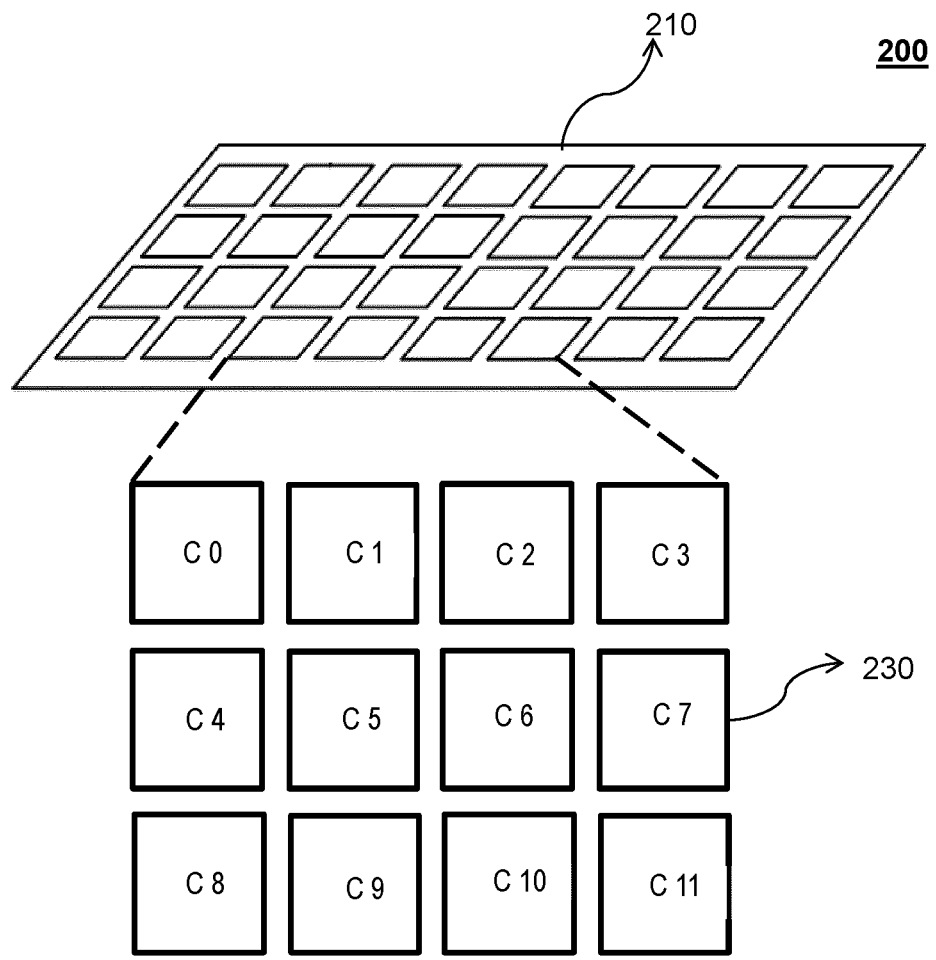
FIG. 2 is the antenna array in accordance with the apparatus of the present disclosure.

FIG. 2 describes the antenna array 230 for transmission and reception of wireless signal (radio frequency signal) in accordance with the apparatus of the present disclosure. The array antenna 230 transfers energy and commands via wireless communication to the at least one wireless marker 170 (shown in FIG. 1). The same set of antenna elements 230 are also configured to receive the signal from the at least one wireless marker 170. Further, each individual antenna element 230 of the array antenna 210 is made by litz wire or a metal layer. Optionally, the elements 230 are fabricated on planar PCB/LTCC substrate with a typical dimension of approximately 4 cm×4 cm. Optionally, the elements 230 may have square, round or hexagonal shape.

Regardless of the shape of the array elements 230, there is a mapping of a position of the implanted wireless marker 140b, with reference to the phased-array antenna. This is achieved by using a dummy cell or a phantom 310 which is made with non-conductive and X-Ray visible material. The use of the phantom 310 allows simulation of an ideal case scenario without any human body impacts on the impedance of the antenna elements 230 (see FIG. 3).

Figure 3:
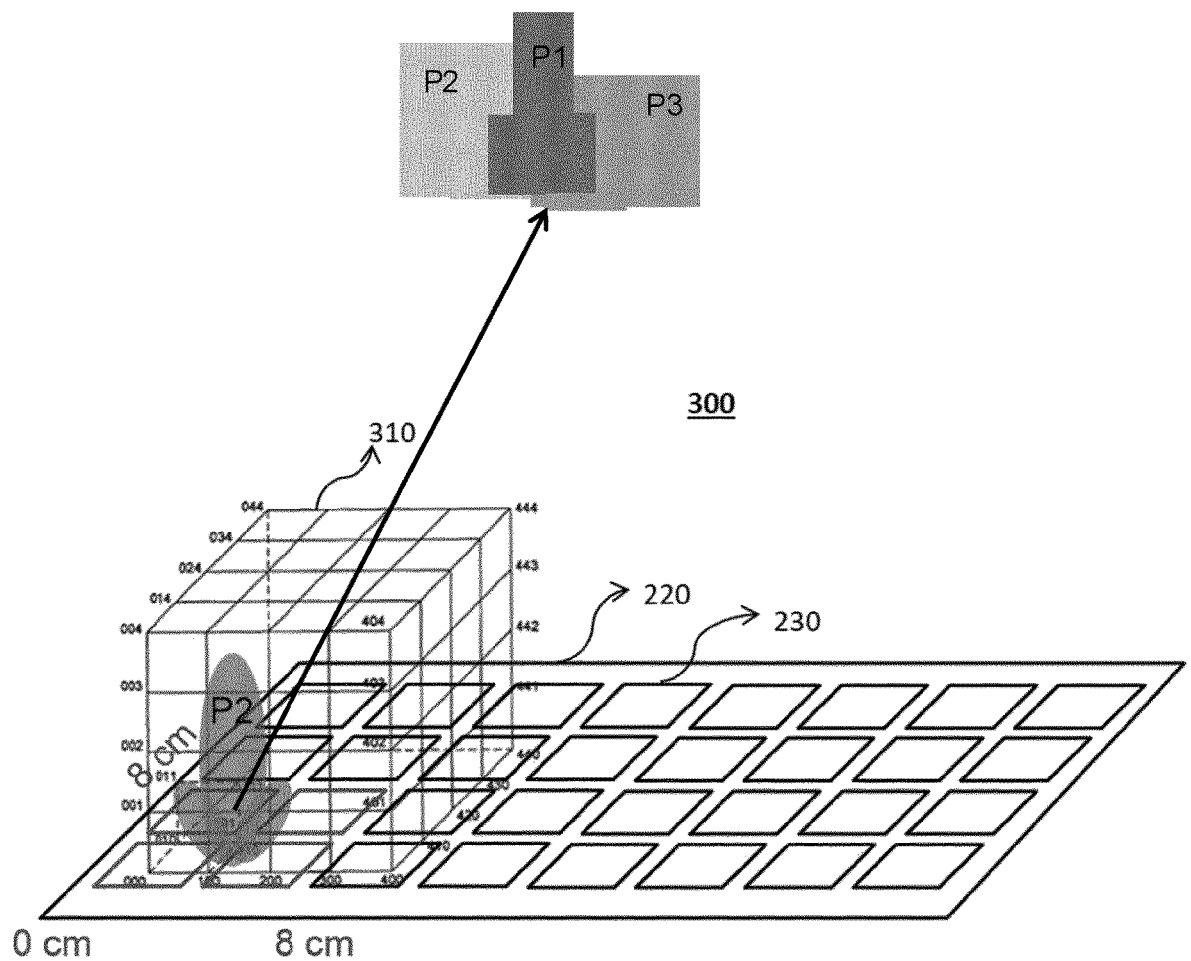
FIG. 3 is a set-up for array antenna calibration in accordance with the apparatus of the present disclosure.

The phantom 310 comprises a plurality of circular holes (for example, using similar diameter as wireless marker, not shown in FIG. 3) that provide positions of locating the wireless marker 140b. The size of the phantom 310 may vary or be similar the size of the complete array antenna 210 or sufficiently large to cover a targeted treatment area (as illustrated in FIG. 3). Optionally, the phantom 310 further comprises a marker on the surface. The markers may be used for a laser scanner or camera to recognize the absolute position and orientation of the phantom.

To calibrate the set-up, the phantom 310 is placed at a defined position on the array antenna 210, for example on top of antenna elements 230. Thereafter, the wireless marker 140b is placed at a pre-defined location inside the phantom 310. An array of antenna elements 230 are selected to transmit a wireless radio frequency signal to the wireless marker 140b located in the phantom 310. For improved accuracy of location, more antenna elements 230 are used with the different phase angle of the wireless signal changed with respect to the antenna element 230 to form a beam (henceforth referred to as beamforming). The strength of a wireless signal from wireless marker received at each antenna element 230 is recorded. The above steps are repeated at different angle (e.g., from P1 to P2, P3, etc) such that the antenna propagation field can cover a larger 3D space. Afterwards, the wireless marker 140b is relocated to next a pre-defined position inside the phantom 310. At the end, the signal strength at each angle is recorded and a complete 3D location map of the wireless marker located at each pre-defined position inside the phantom can be obtained.

System calibration steps can therefore be as follows:

1) Put phantom at defined position on top of phased-array antenna set.

2) Put one wireless marker into pre-defined position inside of phantom. For example, inside the centre (0.5 cm, 0.5 cm, 0.5 cm) of 1st cubic volume located at (1 cm, 1 cm, 1 cm).

3) Select a group of antenna elements to form phased-array antenna such that it could transmit the sufficient wireless power to communicate with wireless marker. Ideally, the more antenna elements used the more tracking accuracy could be reached. However, the maximum power should be still within the Specific Absorption Rate (SAR) as guided by Food and Drug Administration of the United States (e.g., 4 W/kg averaged over whole body, 3.2 W/kg averaged over head). For illustration, the N×N (N=2 in this case) phased-array antenna group is selected to cover an area of 8 cm×8 cm (each antenna elements is 4 cm×4 cm as mentioned before).

4) Apply beamforming with defined angle (e.g. P2 angle) to the selected phased-array antenna group such that the wireless marker can communicate with selected phased-array antenna set. In the meantime, record the received signal strength at each antenna elements (e.g., there are 2×2 antenna elements in this case).

5) Repeat step-4 with different angle (e.g., from P1 to P2, P3, etc) such that the direction of overall antenna propagation field can cover a larger 3D space. In other words, shoot the target (wireless marker) at various angels. At each angle, record the received signal strength at each antenna elements (e.g., there are 2×2 antenna elements in this case).

6) Change the wireless marker to next pre-defined position, for example inside the centre of 2nd cubic volume (e.g., 1.5 cm, 1.5 cm, 1.5 cm). Repeat step 3) to step 5).

7) Redo step 6) again and again. At the end, all the cubic volumes have been placed and tested with one wireless marker.

8) The wireless marker location is a function of the surrounding selected N×N phased-array antenna group, directional angle of propagated EM field (e.g., P1, P2, P3 . . . ), received signal strength at each antenna elements e.g., there are 2×2 antenna elements in this case): f location (N, propagation angle, received signal).

9) Apply data interpolation to neighbour cubic volumes to determine the wireless marker location when it is not actually placed at the centre of each cubic volumes (e.g., 1.3 cm, 1.3 cm, 1.3 cm).

10) In this way, the complete 3D location of wireless marker can be determined by using this reference measurements (or calibration).

When the wireless marker is implanted on a patient 140a, an impedance of both phased array antenna 210 (e.g., Zant) and implanted wireless marker are assumed to be 50 ohms. As the impendence of the antenna element 230 of the wireless marker 170 implanted in the patient is not 50 ohms (due to the natural processes of the body interfering with the passive antenna of the wireless marker) there is an impedance mismatch. This inherent impendence mismatch causes the power amplifiers (present at the transmitter and the receiver elements—not shown) to transmit wireless signal at deteriorated power levels thereby reducing the overall system performance. This is cured by the introduction of an adaptive impedance matching network 570 which not only supports multi-band for different Radio Frequency (RF) Identifiers but also improves the overall system performance under antenna mismatch condition. As a result, the improved signal strength shall be similar as that during the above mentioned system calibration steps.

Figure 4:
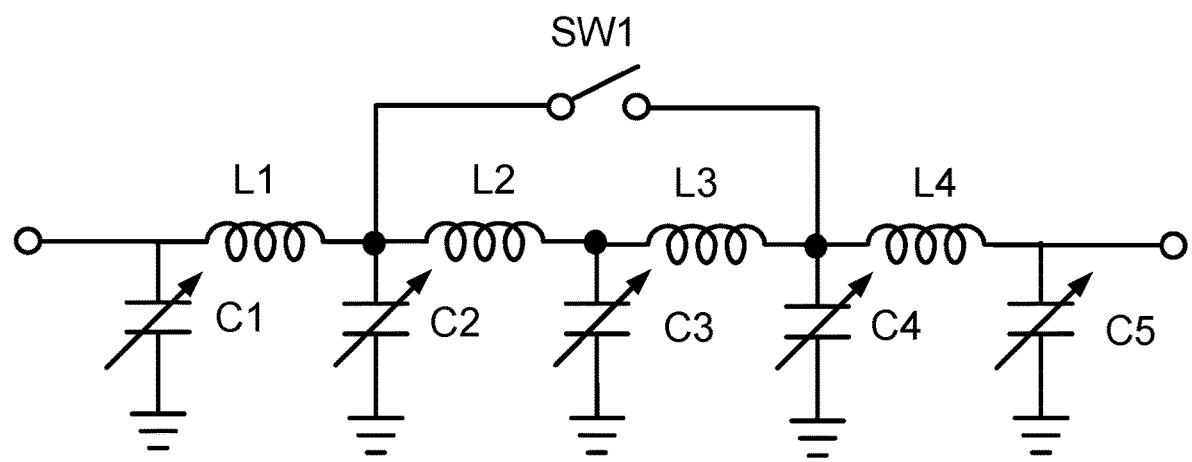
FIG. 4 is the reconfigurable impendence network in accordance with the present disclosure.

The adaptive impedance matching network (MN) 570 is implemented at the wireless marker 140b and at the phased-array antenna 230. For illustration, the proposed MN 570 is based on several tunable capacitors (e.g., C1, C2, C3, C4 and C5) and switches (e.g., SW1) (see FIG. 4). By changing the value of the tunable capacitor, the impedance mismatch condition is corrected close to 50 ohm. For example, since the position of the target implanted wireless marker 140b position is approximately known, the reading gathered from the phantom 310 is used to optimize the capacitor values (e.g., C1-C5) for matching the impedance of that phased array antenna 230 and the wireless marker 140b.

Optionally, the tunable capacitors may be realized with varactors and capacitive switch arrays based on metal-oxide-semiconductor field-effect transistor (MOSFET) switch/radio frequency micro-electromechanical systems (RF-MEMs). The main advantages are their compact size and can be easily integrated inside of MN 570.

Figure 5:
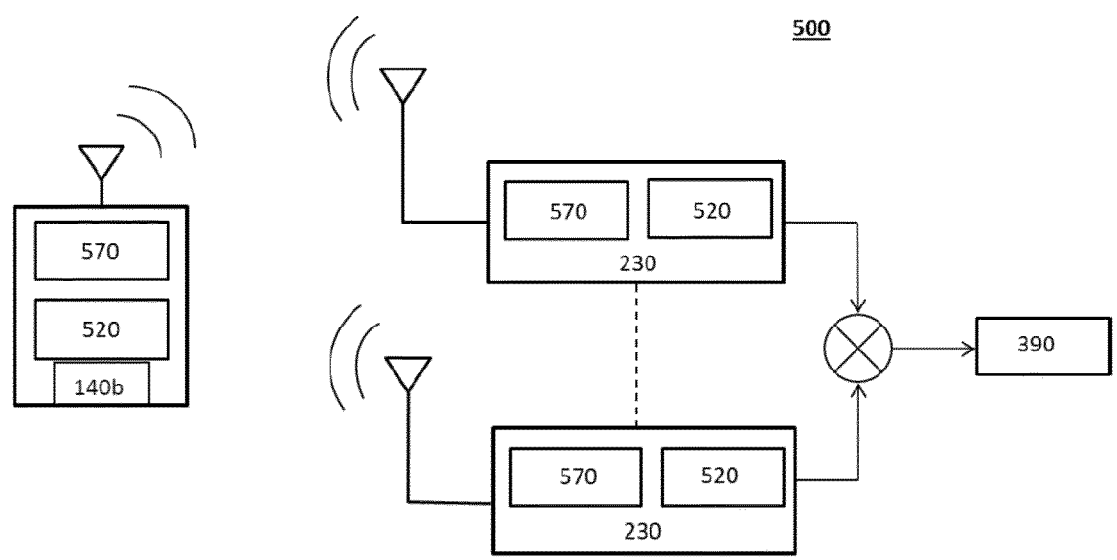
FIG. 5 is a system in accordance with the present disclosure.

FIG. 5 illustrates the combined system 500 for accurately detecting and tracking a wireless marker 140b implanted near the patient's tumor 170 while reducing the EM radiation to which the patient 140a is exposed.

The concept of beamforming is realized by using a large number of separated transmitter and receiver modules 520 combined with impendence matching network 570 in the phased array antenna elements 230 and the wireless marker 140b. The apparatus 500 applies beamforming to the phased-array antenna 230 and uses a selected antenna group to measure the EM field of the wireless marker 140b at various locations. Thereafter, the location system compares the set of actual measurements to sets of reference measurements for various known locations. Based on the comparisons, the location system identifies the set of reference measurements that most closely matches the set of actual measurement values.

The location system then uses a set of reference measurements for known locations near the closest known location to more accurately determine the wireless marker 140*b* location. Therefore, by adjusting the value of each tunable component, the received signal strength at phased-array antenna 230 is optimized to accurately track the wireless marker 140*b* while reducing any EM radiation to the patient 140*a*.

Figure 6:
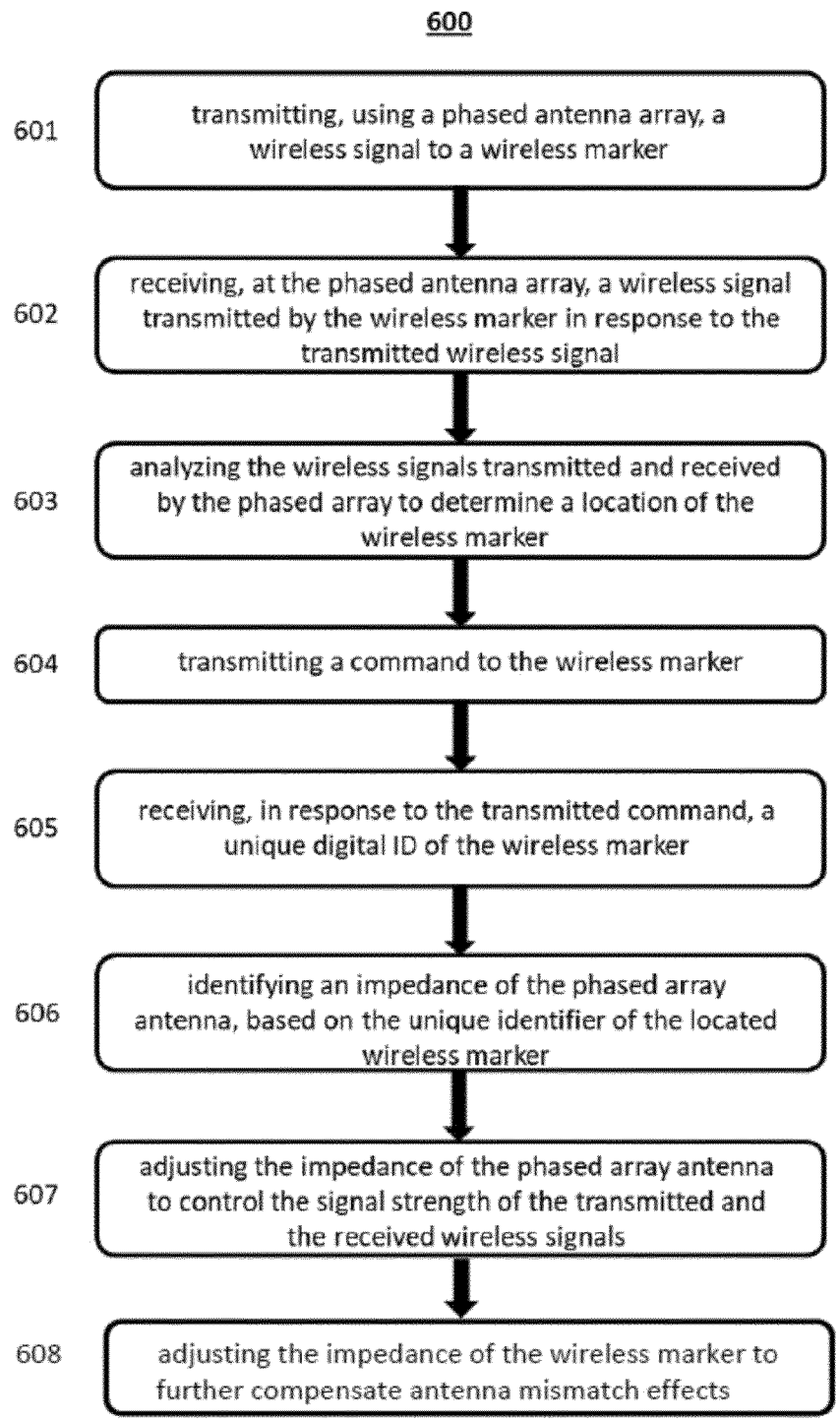
FIG. 6 illustrates a flowchart showing a localization method for determining the position of the wireless marker.

FIG. 6 illustrates the method 600 for determining the location of the wireless marker 140*b* implanted, for example, inside the patient 140*a*, wherein the patient 140*a* is supported by patient table 130, according to some of the example embodiments.

At step 601, the phased array antenna 230 is used to transmit a wireless signal to the implanted wireless marker 140*b*. According to some of the example embodiments, step 601 is preceded by a step according to which an approximate position of the implanted wireless marker 140*b* is mapped and estimated based on an approximate location the tumor 170 and a set of phased array antennas 230 are enabled based on the estimated position of the implanted wireless marked 140*b* during treatment planning.

At step 602, in response to the transmitted wireless signal, a wireless signal is received at the phased array antennas 230 from the implanted wireless marker 140*b*. Thereafter, the transmitted and received wireless signals are analyzed to accurately determine the location of the wireless marker 140*b* (see step 603).

Once the location of the wireless marker 140*b* is determined, a command is transmitted to the wireless marker 140*b*, requesting identification (ID) information (see step 604). According to some of the example embodiments, the identification information is string of number, alphabets, symbols and/or a combination thereof. According to some of the example embodiments, the command may also comprise instructions to further enable or disable the wireless marker 140*b*. According to some of the example embodiments, the command may also comprise instructions to disable other wireless markers present near the identified wireless marker 140*b* to avoid possible signal interference.

At 605, a unique digital ID of the wireless marker 140*b* is received from the wireless marker 140*b* at the phased array antenna 230, in response to the transmitted command. Since the received ID does not only contain digital identification information abut also contains analogy information such as received signal strength at each antenna elements. Based on the received ID of the implanted wireless marker 140*b*, an optimized impendence value of the phased array antenna 230 is determined (step 606). According to some of the example embodiments, the optimized impendence value may be determined based on a table lookup approach which correlates the location of the implanted wireless marker 140*b* with the phased array antenna 230 during mentioned calibration process with phantom.

At step 607, based on the determined optimized impendence value of the phased array antenna 230, the impendence of the enabled phased array antenna 230 is adjusted. By adjusting the impedance of the phased array antenna 230, the signal strength of the transmitted and received wireless signal may be controlled thereby optimizing the EM radiation to which the patient is exposed.

An additional step "608" comprises adjusting the impedance of wireless marker to further compensate antenna mismatch effects. In this way, if the phased array antenna didn't get an increased signal strength from the wireless marker, then the wireless marker needs to continuously adjust the impedance. At the end, the phase array antenna shall receive an increased or at least the same signal strength from the wireless marker.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the claims.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based here on. Accordingly, the embodiments of the present disclosure are intended to be illustrative, but not limiting, of the scope of the disclosure, which is set forth in the following claims.

The invention claimed is:

1. An apparatus for determining a location of a wireless marker for a tumor, the apparatus comprising:
   a phased array antenna, and
   a processor configured to:
     control the phased array antenna to:
       transmit a first wireless signal to the wireless marker;
       receive a second wireless signal transmitted by the wireless marker in response to the transmitted first wireless signal;
       analyze the first and second wireless signals transmitted and received by the phased array antenna to determine a location of the wireless marker;
       transmit a command to the wireless marker;
       receive, in response to the transmitted command, a unique digital ID of the wireless marker;
       identify an impedance of the phased array antenna, based on the unique identifier of the located wireless marker; and
       adjust the impedance of the phased array antenna to control the signal strength of the transmitted and the received first and second wireless signals.

2. The apparatus of claim 1, wherein the processor is configured to:
   activate the wireless marker, using the received unique digital ID, to transmit the second wireless signal in response to the first wireless signal transmitted by the phased array antenna; and
   initialize the phased array antenna based on an approximate location of the active wireless marker; and
   adjust the impedance of the active wireless marker.

3. The apparatus of claim 2, wherein the processor is further configured to:
   receive, in response to the transmitted command, a unique digital ID of a further wireless marker; and
   deactivate the further wireless marker using the received unique digital ID of the further wireless marker.

4. The apparatus of claim 3, wherein the processor is further configured to:
   deactivate the wireless marker using the received unique digital ID of the wireless marker;
   activate the further wireless marker using the received unique digital ID of the further wireless marker; and
   transmit a first wireless signal to the further wireless marker;

receive a second wireless signal transmitted by the further wireless marker in response to the transmitted wireless signal; and analyze the first and second wireless signals transmitted and received by the phased array antenna to determine a location of the further wireless marker.

5. The apparatus of claim 1, wherein the phased array antenna has a planar structure and is configured to be positioned on top of a patient support.

6. The apparatus of claim 5, further comprising a ferromagnetic layer, optionally comprising a plurality of sintered ferrite sheets, wherein the ferromagnetic layer is configured to be placed between the phased array antenna and the patient table; optionally further comprising an insulating mattress layer wherein the insulating mattress is configured to be placed between the patient and the phased array antenna.

7. The apparatus of claim 5, wherein the planar structure of the phased array antenna is implemented on a printed circuit board and/or a low temperature cofired ceramic.

8. The apparatus of claim 1, wherein the phased array antenna is configured to operate between 110 KHz and 2.5 GHz.

9. The apparatus of claim 1, wherein the wireless marker is configured to be implanted within the body of a patient or to be attached to a surface of the patient.

10. A method for determining a location of a wireless marker for a tumor, the method comprising:

transmitting, using a phased antenna array, a first wireless signal to the wireless marker;

receiving, at the phased antenna array, a second wireless signal transmitted by the wireless marker in response to the transmitted first wireless signal;

analyzing the first and second wireless signals transmitted and received by the phased array antenna to determine a location of the wireless marker;

transmitting a command to the wireless marker;

receiving, in response to the transmitted command, a unique digital ID of the wireless marker;

identifying an impedance of the phased array antenna, based on the unique identifier of the located wireless marker; and adjusting the impedance of the phased array antenna to control the signal strength of the transmitted and the received first and second wireless signals.

11. The method of claim 10, further comprising:

Activating the wireless marker using the received unique digital ID, to transmit the second wireless signal in response to the first wireless signal transmitted by the phased array antenna; and initializing the phased array antenna based on an approximate location of the active wireless marker; and adjust the impedance of the active wireless marker.

12. The method of any of claim 11, further comprising:

receiving, in response to the transmitted command, a unique digital ID of a further wireless marker; and deactivating the further wireless marker using the received unique digital ID of the further wireless marker.

13. The method of claim 12, further comprising:

deactivating the wireless marker using the received unique digital ID of the wireless marker;

activating the further wireless marker using the received unique digital ID of the further wireless marker; and transmitting a first wireless signal to the further wireless marker;

receiving a second wireless signal transmitted by the further wireless marker in response to the transmitted wireless signal; and analyzing the first and second wireless signals transmitted and received by the phased array antenna to determine a location of the further wireless marker.

\* \* \* \* \*